(12) United States Patent
Coluni et al.

(10) Patent No.: US 8,682,688 B1
(45) Date of Patent: Mar. 25, 2014

(54) SYSTEMS, METHODS, AND SOFTWARE FOR SUPPORTING CONSUMER HEALTHCARE DECISIONS

(75) Inventors: Barbara Coluni, Ann Arbor, MI (US);
Doug Schneider, Cincinnati, OH (US);
Mark Gillespie, Northville, MI (US)

(73) Assignee: Truven Health Analytics Inc., Ann Arbor, MI (US)

( * ) Notice: Subject to any disclaimer, the term of this patent is extended or adjusted under 35 U.S.C. 154(b) by 0 days.

(21) Appl. No.: 12/321,129

(22) Filed: Jan. 14, 2009

Related U.S. Application Data

(60) Provisional application No. 61/011,037, filed on Jan. 14, 2008.

(51) Int. Cl.
*G06Q 10/00* (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| | | | | |
|---|---|---|---|---|
| 7,671,868 B2 * | 3/2010 | Morita et al. | | 345/581 |
| 7,734,483 B1 * | 6/2010 | Smith et al. | | 705/3 |
| 2007/0011026 A1 * | 1/2007 | Higgins et al. | | 705/2 |
| 2007/0276702 A1 * | 11/2007 | Dani | | 705/3 |

* cited by examiner

*Primary Examiner* — Hiep V Nguyen
(74) *Attorney, Agent, or Firm* — Plumsea Law Group, LLC

(57) ABSTRACT

The present inventor(s) conceived of, among other things, a consumer healthcare portal to help consumers make well-informed healthcare decisions. One exemplary portal incorporates existing healthcare claims data from payers to provide personalized offerings around health plan selection and treatment options guidance. This data also provides the ability for consumers to assess the effectiveness of various physicians in their plans. Additionally, the exemplary portal provides a consumer messaging capability that facilitates automatic transmission of personalized healthcare communications geared to change individual consumer behavior.

26 Claims, 14 Drawing Sheets

Table 1: Input/Output/Manipulation/Error Handling

Conditions: I/O Summary

| Display Information | Input Sources | Input Fields | Manip. Of Input/Lookup | Output | Error Handling |
|---|---|---|---|---|---|
| Based on the current person (person ID) identify the following: | | | | | |
| Condition Description | Medical Claims, PHR | Unique Principal and Secondary Dx Codes (Claims); Condition (PHR) | Translate dx codes to diagnosis group; lookup layman condition description for condition group. | Layman Condition Description | If no condition found, diplay "Unknown condition" |
| Last Treated On | Medical Claims | Date of Service | For all claims with the same assigned condition, lookup the most recent claim's service date | Date: In MM/DD/YYYY format | If no date or source is from PHR, leave blank |
| Condition Education Link | Medical Claims; Condition Description; Health Encyclopedia | Dx Code or Condition Description | Create link to Health Education article. See I/O narrative for more details. | Link to Condition Article or link to search | See I/O Notes for more details. |
| Condition Details | Medical Claims, PHR | Diagnosis Group; Dx Code or Condition Description | Create link to list the detailed claims for that condition located in Patient Health Statement (PHS). | Link to condition in PHS | If no claim is found in PHS, provide message that no claim found for this medication. Optionally, advise user to check PHR for medication. |

Conditions: I/O Notes

FIGURE 4

Table 2: Input/Output/Manipulation/Error Handling
Medication: I/O Summary

| Display Information | Input Sources | Input Fields | Manip. Of Input/Lookup | Output | Error Handling |
|---|---|---|---|---|---|
| Based on the current person (person ID) identify the following: | | | | | |
| Medication Description | Drug Claims, PHR | NDC Code or PHR Medication Name | If using NDC, lookup description; if source is PHR, use description directly. | Medication description | If no medication found, for NDC, display "Unknown medication"; suppress education link but create link to underlying claims so that problem can be traced to specific claim. |
| Last Refill | Drug Claims | Date of Service | Identify "most recent" claim: For all claims with the same NDC, use the most recent claim's service date | Date: In MM/DD/YYYY format | If no date or source is from PHR, leave blank |
| Days Supply | Drug Claims | Days Supply | Using most recent claim for this medication (NDC), lookup days supply | | If source is from PHR, leave blank |
| Next Refill | Drug Claims | Days Supply, Number of Refills | Compute date: If Number of Refills > 0 then Next Refill = Last Refill date + days supply. Convert to new date. If Number of Refills = 0 or missing, Next Refill is missing. | Date: In MM/DD/YYYY format | If no date or source is from PHR, leave blank |
| Medication Education Link | Drug Notes | NDC Code or Medication Description (PHR) | Create link to Health Education article. See I/O narrative for more details. | Link to article or link to search | See I/O narrative for more details. |
| Medication Details | Drug Claims, PHR | NDC Code, Date of Service | Create link to the associated detailed claim(s) located in Patient Health Statement (PHS). | Link to most recent service for this medication in PHS | If no claim is found in PHS, provide message that no claim found for this medication. Optionally, advise user to check PHR for medication. (might link to PHR but could be confusing to have some links to PHS and some to PHR) |
| Flag/Link: Generic Equivalent | Drug Notes | NDC Code | Search Drug repository by NDC. Retrieve whether generic equivalent available and list of generic equivalents and their associated NDC codes. | Display flag if equivalent available; display link/rollover with list of equivalents and links to their drug notes. | Suppress flag if no NDC for med or no equivalent returned from search. |
| Flag/Link: Drug Interactions | Drug Claims, Drug Interaction Checker | NDC Code for each "active" drug | - Identify "active" drugs (those drugs currently in use. See "Methods" section below) | | |
| Explicit Link: Drug Interaction Checker | Drug Interaction Checker | List of "active" drugs (NDC Code and Description), age, gender | Create link to Drug Interaction Checker tool. Pass list of "active drugs". Prepopulate Drug Interaction Checker with each active drug. | Link to pre-populated Drug Interaction Checker | If no active drugs, pass age and gender only; |

FIGURE 5

Table 3: Input/Output/Manipulation/Error Handling

Care History: I/O Summary

| Display Information | Input Sources | Input Fields | Manip. Of Input/Lookup | Output | Error Handling |
|---|---|---|---|---|---|
| Based on the current person (person ID) identify the following: | | | | | |
| Service Type | Claims/PHS | Type of Service | Group claims by broad service type categories (used same categories as those in PHS). | Service Type Description | If no claims, suppress graph. Display message that no healthcare claims found. |
| Date Data Point | Claims, PHS | Date of Service | For each date of service and Service Type group, plot data point | Plot point on chart by type of service and date | |
| Service Type Details Link | Claims, PHS | Type of Service, Date of Service | For each Service Type description, create link to list the detailed claims for those services located in Patient Health Statement (PHS). | Link to claims detail in PHS for these service types across all dates. | |
| Data Point Info | Claims, PHS | Service Type, Date of Service, provider ID, Condition Description or Drug Name | Based on elements set for each data point (above), create mini-summary of that claim: Date of Service, Type of Service, provider name (based on provider ID), Condition if visit or Medication if Prescription. | Quick Summary of Service | |
| Data Point Link | Claims, PHS | Service Type, Date of Service | Provide link to PHS service on this date | Link to this claim in the PHS | |

FIGURE 6

| Key health statistics | | | |
|---|---|---|---|
| Health stat | Date | *Value | Target range |
| Blood pressure | (07/01/07) | 142 / 93 mm/Hg ↓ | <120 / <80 mm/Hg |
| Blood sugar | (06/28/07) | 98 ↑ | <100 mg/dL |
| BMI | (06/15/07) | 24.9 ↓ | 18.5 – 24.9 |
| Cholesterol Total | (07/07/07) | 240 mg/dL ↓ | 200 – 210 mg/dL |
| Cholesterol HDL | (07/07/07) | 39 mg/dL ↑ | 40 – 60 mg/dL |
| Cholesterol LDL | (07/07/07) | 161 mg/dL ↓ | <100 mg/dL |
| Pulse | (06/15/07) | 79 BPM ↓ | 60 – 100 BPM |
| Height | (06/15/07) | 5' 4" | |
| Weight | (06/15/07) | 145 lbs ↓ | 120 – 130 lbs |

* Statistic values that are significantly outside the target range are shaded

Table 4: Vital Signs 1

FIGURE 7

Table 5: Vital Signs 2

Table 6: Input/Output/Manipulation/Error Handling

My Stats: I/O Summary

| Display Information | Input Sources | Input Fields | Manip. Of Input/Lookup | Output | Error Handling |
|---|---|---|---|---|---|
| Based on the current person (person ID) and for each health care stat provide the following information: | | | | | |
| Health Stat Description | CapMed PHR | Health Stat | | Description | |
| Value | CapMed PHR | Value, Date | Use value from most recently recorded date for that metric. See notes below | Value | Leave blank if there is no value found for the metric across all dates. |
| Target Range | New method/lookup, User Profile/Claim | Vital Stat Lookup Table, Age, Gender | For each vital sign, look standard vital sign (some may be age/gender specific) | Target lower and upper range values | Leave blank if no targets defined or found |
| Out of Range Flag | | Value, Target Range | Visually indicate those stats that are out of the target range | Visual indicator for out of range values | |
| Stat Trend | Vital Sign "history" for stat | Value, Date | For most current value of this stat, look for next most recent (prior) recorded value. If current value is higher than prior, trend is up. If current value is lower, trend is down. If values are the same or there is no prior value, leave trend as unrecorded. | Trend indicator (visual or textual) | Leave blank if no history for stat or no change. |
| Date | CapMed PHR | Date Recorded | Use date of most recently recorded entry for that stat | Date in MM/DD/YYYY format | |
| Stat Education Link | Health Stat Description, Health Education Content | Stat Description, Health Encyclopedia | Create link to education article for this stat (follow relevancy rules defined earlier) | Link to article on current stat | Same as for Condition content links. |
| PHR Vital Link | CapMed PHR | PHR Section: Medical Details | Vitals and Profile | Create link to PHR Vital Sign page | Link to PHR Vital Sign | |

FIGURE 9

Table 7: Sample Design from Demo

FIGURE 10

Table 9: Input/Output/Manipulation/Error Handling
My Expenses: I/O Summary

Based on the current person (person ID) and member ID, provide the following:

| Display Information | Input Sources | Input Fields | Manip. Of Input/Lookup | Output | Error Handling |
|---|---|---|---|---|---|
| Date Filter – Start Date | Claims, PHS | Date of Service | Oldest date of service in claims for this member (self and dependents if any) – Use with End Date to filter list of PHS-eligible claims. Actual date should be the first day of month for starting date of range. | Start date for display in filter (mmm/yyyy format) Example: Jan 2007 (actual Jan 01, 2007) | |
| Date Filter – End Date | Claims, PHS | Date of Service | Most recent date of service in claims for this member (self and dependents if any). Use with End Date to filter list of PHS-eligible claims. Actual date should be last day of month for end date of range. | End Date for display in filter (mmm>/yyyy format) Example: Dec 2007 (actual Dec 31, 2007) | |
| Condition Filter | PHS, Claims | Conditions (See My Conditions above) | List of unique conditions for this member (self and dependents) | List of unique conditions | |
| Category of Service Description | PHS | Service Category | Lookup Description | Description | |
| Service Type | PHS, Member ID | Service Type | Use PHS to find | Service Type Description | |
| Service Type Details Link | PHS | Type of Service, Date of Service | For each Service Type description, create link to list the detailed claims for those services located in Patient Health Statement (PHS). | Link to claims detail in PHS for these service types across all dates. | |
| | PHS | Total Costs | Sum of total costs for all services for member | $n,nnn | |
| Expenses "Grand Total" for Plan/Employer | PHS | <> Total Costs Paid by Plan | Sum of total costs paid by plan for all services for member | $n,nnn | |
| Expenses "Grand Total" for "You" | PHS | <> Total Costs Paid by member | Sum of total costs paid by member for all services for member | $n,nnn | |
| Expenses Row Totals by Service Type: User, Dependents | PHS | Total Costs, Service Type, current person ID, dependent ID (see open issues under Methods) | - Sum total costs by Service Type and current person.<br>- Sum total costs by Service Type and all other dependents for the current person (if any)<br>- Row total: Sum total costs for current person and dependents in row | $n,nnn | If no dependents, only show "Total" (suppress totals for "You" and "Dependents") |
| Usage Row Totals by Service Type: User, Dependents, Total | PHS | | - Count of Services by Service Type and current person.<br>- Count of Services by Service Type and all either dependents for the current person (if any)<br>- Row total: Sum counts of Services for current person and dependents in row | Format: n,nnn | |
| Expenses Grand Total: User, Dependents, Total | PHS | Total Costs, Service Type, current person ID, dependent ID (see open issues under Methods) | --Sum Expenses across Service Type for current person; Sum Expenses across Service Type for dependents; Sum current person and dependent for Total (should equal Expenses "Grand Total" for "You") | Format: $n,nnn | If no dependents, only show "Total" (suppress totals for "You" and "Dependents") |
| Usage Grand Total by Service Type: User, Dependents, Total | PHS | | Sum Services across Service Type for current person; Sum Services across Service Type for dependents; Sum current person and dependent for Total | Format: n,nnn | |

FIGURE 12

Table 10: Diagnosis Codes:

| DX_CD | DX | DX_COND | CLINICAL_COND | Layperson Terminology |
|---|---|---|---|---|
| 41001 | AMI Anterolateral, Init | Acute Myocardial Infarct | Coronary Artery Disease | Heart Attack |
| 41011 | AMI Anterior Wall, Init | Acute Myocardial Infarct | Coronary Artery Disease | Heart Attack |

FIGURE 13

Table 11: Procedure Codes:

| PROC_CD | PROC_SYSTEM | PROC | Layperson Terminology |
|---|---|---|---|
| 45355 | CPT | Surgical Colonoscopy | Colonoscopy |
| 45378 | CPT | Diagnostic Colonoscopy | Colonoscopy |
| G0102 | HCPCS | Prostate CA Screening; | Prostate Cancer Screening test |
| G0103 | HCPCS | Psa, Total Screening | Prostate Cancer Screening test |

FIGURE 14

Table 12: Drug Codes:

| PRODUCT_NAME -- Drug | Layperson Terminology (Drug Brand Name) |
|---|---|
| Omeprazole | Prilosec |
| Valsartan | Diovan |

FIGURE 15

Table 13: Diagnosis Codes:

| DX_CD | DX | DX_COND | CLINICAL_COND | Layperson Terminology |
|---|---|---|---|---|
| 41001 | AMI Anterolateral, Init | Acute Myocardial Infarct | Coronary Artery Disease | Heart Attack |
| 41011 | AMI Anterior Wall, Init | Acute Myocardial Infarct | Coronary Artery Disease | Heart Attack |

FIGURE 16

Table 14: Procedure Codes:

| PROC_CD | PROC_SYSTEM | PROC | Layperson Terminology |
|---|---|---|---|
| 45355 | CPT | Surgical Colonoscopy | Colonoscopy |
| 45378 | CPT | Diagnostic Colonoscopy | Colonoscopy |
| G0102 | HCPCS | Prostate CA Screening; | Prostate Cancer Screening test |
| G0103 | HCPCS | Psa, Total Screening | Prostate Cancer Screening test |

FIGURE 17

Table: 15 Drug Codes:

| PRODUCT_NAME – Drug | Layperson Terminology (Drug Brand Name) |
|---|---|
| Omeprazole | Prilosec |

FIGURE 18

SYSTEMS, METHODS, AND SOFTWARE FOR SUPPORTING CONSUMER HEALTHCARE DECISIONS

RELATED APPLICATIONS

The present application claim priority to U.S. Provisional Patent Application 61/011,037, which was filed on Jan. 14, 2008 and which is incorporated herein by reference.

COPYRIGHT NOTICE AND PERMISSION

A portion of this patent document contains material subject to copyright protection. The copyright owner has no objection to the facsimile reproduction by anyone of the patent document or the patent disclosure, as it appears in the Patent and Trademark Office patent files or records, but otherwise reserves all copyrights whatsoever. The following notice applies to this document: Copyright © 2007, Thomson Reuters Healthcare, Inc.

TECHNICAL FIELD

Various embodiments of the present invention concern health care management systems, particularly consumer-oriented healthcare websites that help consumers make better healthcare decisions.

BACKGROUND

Over the last decade, large and consistent increases in health care costs have driven health-care payers (employers, health plans, state and federal government) to seek methods of controlling expenses. The leading cost-control trend today is to provide economic incentives for consumers to actively participate in making their health care decisions. However, the present inventor has recognized that the success of this type of cost control hinges on the quality of healthcare decisions that incentivized consumers will make. Poor decisions may undermine or limit any promise of actual cost control.

Accordingly, the present inventors recognized a need for tools that help consumers make healthcare decisions.

SUMMARY

To address this and/or other needs, the present inventor conceived of, among other things, a consumer healthcare portal to help consumers make well-informed healthcare decisions. One exemplary portal incorporates existing healthcare claims data from payers to provide personalized offerings around health plan selection and treatment options guidance. This data also provides the ability for consumers to assess the effectiveness of various physicians in their plans. Additionally, the exemplary portal provides a consumer messaging capability that allows for personalized healthcare communications geared to change individual consumer behavior.

BRIEF DESCRIPTION OF DRAWINGS

FIG. 2 is a facsimile of an exemplary graphical user interface portion of system 100, which corresponds to one or more embodiments of the present invention.

FIG. 3 is a facsimile of another exemplary graphical user interface portion of system 100, which corresponds to one or more embodiments of the present invention.

FIGS. 4-18 show exemplary graphical user interface portions of system 100 in table form, which correspond to one or more embodiments of the present invention.

DETAILED DESCRIPTION OF EXEMPLARY EMBODIMENT(S)

This description, which incorporates the figures and appended claims, describes one or more specific embodiments of one or more inventions. These embodiments, offered not to limit but only to exemplify and teach the inventive subject matter, are shown and described in sufficient detail to enable those skilled in the art to implement or practice the invention(s). Thus, where appropriate to avoid obscuring the invention(s), the description may omit certain information known to those of skill in the art.

Exemplary Consumer Healthcare Decision Support System

Figure 1:
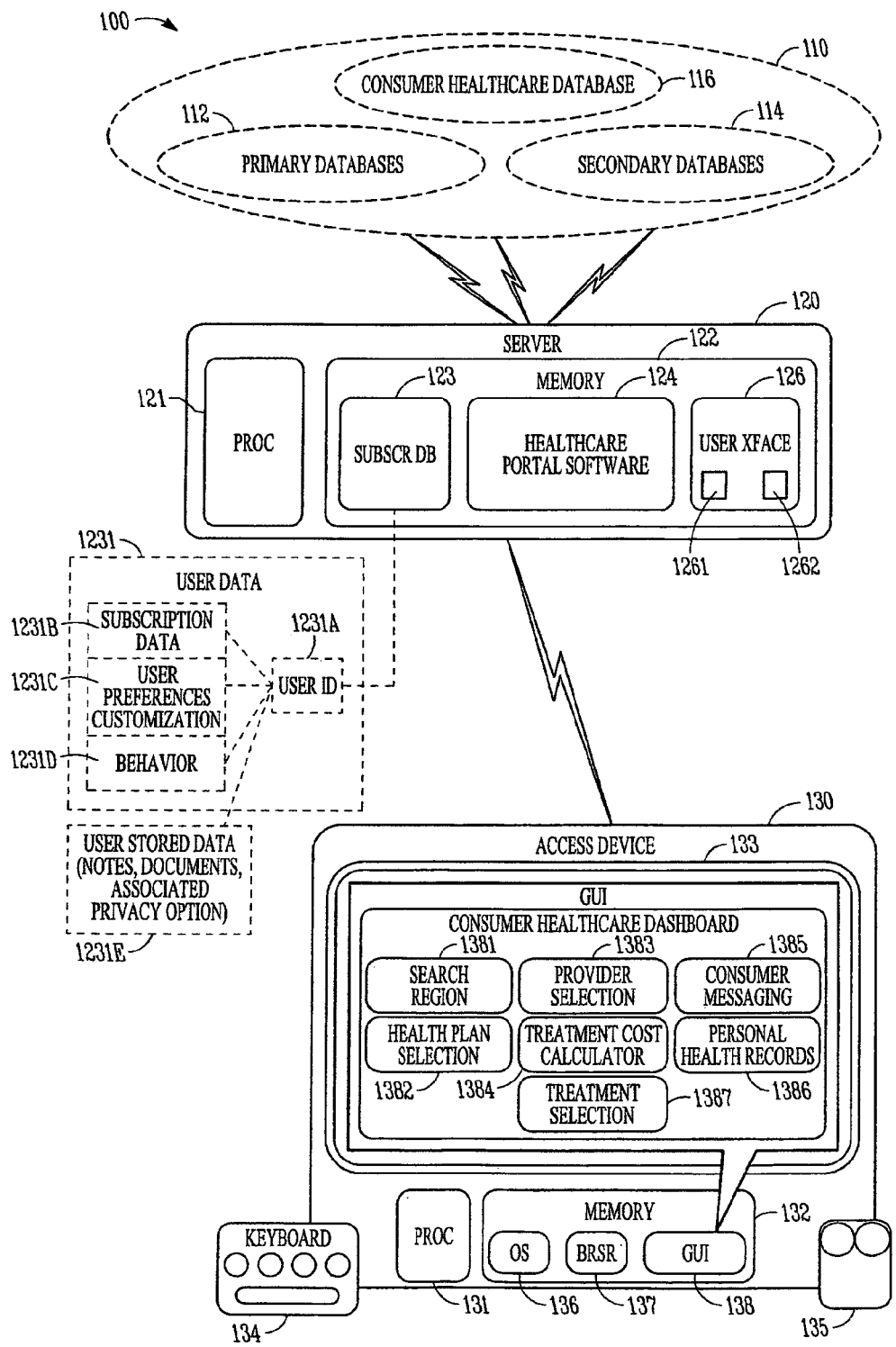
FIG. 1 is a block diagram of an exemplary online consumer healthcare decision support system 100, which corresponds to one or more embodiments of the present invention.

FIG. 1 shows an exemplary online consumer healthcare decision support system 100. System 100 includes one or more healthcare databases 110, one or more servers 120, and one or more access devices 130.

Healthcare databases 110 includes a set of one or more databases which contain data as described herein for access via server 120. Databases 110, which take the exemplary form of one or more electronic, magnetic, or optical data-storage devices, include or are otherwise associated with respective indices (not shown). Each of the indices includes terms and phrases in association with corresponding document addresses, identifiers, and other conventional information. Databases 110 are coupled or couplable via a wireless or wireline communications network, such as a local-, wide-, private-, or virtual-private network, to server 120.

Server 120, which is generally representative of one or more servers for serving data in the form of webpages or other markup language forms with associated applets, ActiveX controls, remote-invocation objects, or other related software and data structures to service clients of various "thicknesses." More particularly, server 120 includes a processor module 121, a memory module 122, a subscriber database 123, a primary search module 124, metadata research module 125, and a user-interface module 126.

Processor module 121 includes one or more local or distributed processors, controllers, or virtual machines. In the exemplary embodiment, processor module 121 assumes any convenient or desirable form.

Memory module 122, which takes the exemplary form of one or more electronic, magnetic, or optical data-storage devices, stores subscriber database 123, and a healthcare portal software module 124.

Subscriber database 123 includes subscriber-related data for controlling, administering, and managing pay-as-you-go or subscription-based access or use of healthcare portal software and data module 124. In the exemplary embodiment, subscriber database 123 includes one or more user preference (or more generally user) data structures. In the exemplary embodiment, one or more aspects of the user data structure relate to user customization of various aspects of healthcare portal.

Healthcare portal software module 124 includes machine readable and/or executable instruction sets and related data or for implementing a healthcare portal as described herein. For example, module 124 includes search engines, calculation engines. Additionally, module 124 wholly or partly defines web-based graphical user interfaces and related functionality over a wireless or wireline communications network on one or more accesses devices, such as access device 130.

Access device 130 is generally representative of one or more access devices. In the exemplary embodiment, access device 130 takes the form of a personal computer, workstation, personal digital assistant, mobile telephone, or any other device capable of providing an effective user interface with a server or database. Specifically, access device 130 includes a processor module 131 one or more processors (or processing circuits) 131, a memory 132, a display 133, a keyboard 134, and a graphical pointer or selector 135.

Processor module 131 includes one or more processors, processing circuits, or controllers. In the exemplary embodiment, processor module 131 takes any convenient or desirable form. Coupled to processor module 131 is memory 132.

Memory 132 stores code (machine-readable or executable instructions) for an operating system 136, a browser 137, and a consumer healthcare dashboard graphical user interface (GUI) 138. In the exemplary embodiment, operating system 136 takes the form of a version of the Microsoft Windows operating system, and browser 137 takes the form of a version of Microsoft Internet Explorer or Firefox. Operating system 136 and browser 137 not only receive inputs from keyboard 134 and selector 135, but also support rendering of GUI 138 on display 133. Upon rendering, GUI 138 presents data in association with one or more interactive control features (or user-interface elements). (The exemplary embodiment defines one or more portions of interface 138 using applets or other programmatic objects or structures from server 120.) The exemplary dashboard is tailored for payer sponsored consumer decision support, providing a comprehensive web-based application suite that includes health plan selection tools; provider selection tools; treatment cost calculation tools; consumer messaging tools, personal health records tools, and treatment selection tools.

More specifically, graphical user interface 138 defines or provides one or more display regions, such as a query or search region 1381, a health-plan selection 1382, a provider selection region 1383, a treatment cost calculator region 1384, a consumer messaging region 1385, a personal health records region 1386, and a treatment selection region 1387. Although FIG. 1 may suggest all regions of the interface being simultaneously displayed, some embodiments present them at separate times.

Query or search region 1381 is defined in memory and upon rendering includes one or more interactive control features (elements or widgets), such as a query input region, a query submission button, and a results display region (not shown in this Figure).

Health plan selection region 1382 provides tools that compare health plan coverage and other attributes (e.g., open networks, quality of care) and estimate total employee or member costs based on prior healthcare utilization. These tools are also important components in the need for healthcare purchasers to encourage consumers to enroll in health plans that reduce purchaser costs, often in exchange for the consumer receiving a health savings account benefit that enables them to potentially save money and invest for the future.

Provider selection region 1383 provides information on hospital, physician, and other care providers. These tools enable users to select based on type of provider, location, network participation, cost and quality.

Treatment cost calculator region 1384, closely related to health plan selection, provides consumer's tools that help them make appropriate financial decisions in taking increased responsibility for their own healthcare expenditures and management of their health savings account and also to manage their Health Savings Account. Treatment cost advisors that enable consumers to compare their projected out-of-pocket expenditures for major healthcare events, such as elective knee surgery, by provider, or for a specific condition, e.g., diabetes, are another important financial management capability. More advanced treatment cost calculators will also understand the consumer's health plan benefit design and year-to-date financial experience, so that out-of-pocket expenditures can be more accurately estimated. The treatment cost calculator is also highly valuable to physicians, who can use it to determine how likely they are to be paid for services before the treatment is actually rendered.

Consumer messaging region 1385 is provided in recognition that simply making data available for a consumer to access on his or her own initiative is likely to result in a dismal utilization rate. Thus, consumer messaging region 1385 displays personalized, relevant and timely information that is "pushed" to individual consumers, and thus has a better chance of actually modifying consumer behavior. For example, it is an accepted best practice that patients who have heart attacks should be prescribed a type of medication known as a beta blocker. Thus, some embodiments detect whether claims came through indicating a heart attack without a corresponding beta blocker prescription, and in response display a message in region 1385 for the individual suggesting that they ask their doctor about the prescription. The message could also be copied to the patient's physician of record, assuming HIPAA regulations were satisfied.

Personal health records region 1386 displays a comprehensive view of the consumer's profile including demographic information, self-reported health risk assessment, medical and drug history, emergency contacts, chronic or acute disease, etc. Capabilities to authorize healthcare providers and family members to view personal health records, as well as "delegate" access to authorized physicians and caregivers, are an important capability for consumers, which is also provided. Personal health records are automatically and intelligently populated with health claims history.

Treatment selection region 1387 provides information, menu, and selection features that enable consumers to select appropriate care options, customized to the consumer's healthcare status and consistent with evidence-based guidelines. This region provides access to referential databases on diseases, treatments and drug therapies. Sound information on treatment options is especially important to consumers with chronic illnesses, who frequently face major health decisions with significant life consequences. (Treatment option information is widely available in the market, including information from third-party provider.)

Exemplary Consumer Healthcare Dashboard (or Portal)

The exemplary Consumer Dashboard (or consumer healthcare graphical user interface) is the web home page or gateway providing access to the health and wellness management tools available in the exemplary system (also referred to herein as Consumer Decision Support System (CDSS)). The dashboard also serves as the default navigation framework for the CDSS. CDSS is design for purchase by Employers and Health Plans (customers) for use by their employees/enrollees (users).

The primary goal of the dashboard is to engage users in managing the health, wellness and health care costs of themselves and/or other loved ones. To this end, the exemplary dashboard provide users with:

A quick-glance of the state of a user's health/health care spending.

Personalized, actionable alerts about key health issues related to that person's relevant preventative services (e.g., annual physical, mammogram, and immunizations), disease management, medications, upcoming tests, etc.

Messages/reminders created by the user or posted by the customer.

Access to more detailed tools that track healthcare events via a Personal Health Care record (PHR) and/or a summary of medical insurance claims.

Personal health information that can be printed and/or electronically shared.

Access to research tools that allow the user to—
- Investigate and learn about diseases, procedures, medications, traditional and alternative treatment options
- Monitor, track, and suggest wellness activities.
- Select hospitals and physicians (providers) based on both cost and quality metrics.

Access to healthcare spending tools that predict treatment costs and future medical insurance options, and summarize current healthcare spending.

Reliable news around healthcare issues of interest to the user.

Access to personalization tools:
- "Manual Entry" tools that allow the users to create a profile (register) information about themselves, insurance coverage, contact information, and day-to-day usage needs.
- "Smart" personalization tools that the product employs to understand users, their usage patterns, key healthcare issues and then customizes content based on that discovery.

The exemplary dashboard allows customers, for example healthcare payers, the option to use the dashboard as is or to brand it and the linked content to match their desired look and feel (new "skins"). Optionally, the customers can opt to purchase individual modules and develop their own dashboard and hosting platform. In this case the customer will need provide user "registration" information required by the individual system components. In the initial release of the CDSS, user content will be available in the categories (modules) noted below. Customers will be able to opt to include or exclude each of these modules/sub-modules. Customers will be able to substitute content modules in place of the default modules (e.g., use Mayo Clinic health care articles/encyclopedia). More content and customization detail is provided later in this document.

Content available from the dashboard can be broken into a few different categories:

My Health at a Glance:
- Health status/spending overview for the current user: Current disease conditions, drugs, key vital signs, spending. Summaries are displayed directly on the dashboard.
- This content links to more detailed healthcare management tools:
  - My Health in Detail: The user's Personal Health Record (optional module) and Personal Health Statement (claims overview and detail)
- Links to health education information is personalized to reflect the current user's healthcare history and interests. For example, customized links from the user's conditions or drugs to related articles will provide personalized educational resources. The links are directed to the detailed Health Education modules (below).
- Links to recent Healthcare News headlines based on user's preferences and health issues Alerts and Messages: personalized health maintenance reminders or user/customer defined messages Access to Health Education and Healthy Living Tools:
- Links to general health education and health management tools (e.g., Adam/Micromedex surgery, drug content; Consumer Treatment Cost Calculator, provider selection tools or links customer-defined content).
- Healthcare News feeds based on user's preferences and conditions Healthcare Management Tools—Links to:
- Personal Health Record (PHR)
- Personal Health Statement Access to "Housekeeping Modules": Links to support modules such as Help, user selection, user profiles/registration information, terms of use agreement, contact information, etc, "contact us".

User Greeting and Logout
- Consider adding a "Getting Started" page to provide a quick overview of key features, first steps (e.g., profile), getting data into PHR ( ) . . . .

The Consumer Insights Database provide data from and/or access to a core set of data sources captured about each person:

Person and Household Information, such as Person ID, Household ID, Name, Address, E-mail, Demographic data Medical claims, such as conditions, risk score, costs Prescription drug claims e.g. products, # of scripts Eligibility, e.g. Plan, coverage, Retired status, Terminated status)

Campaign history and response data, such as history to be tracked by platform, responses in part to be fed back from campaign execution/delivery activities Message content, e.g. relationship between an individual, a campaign, and the specific message content the individual received through that campaign)

Consumer segmentation information
PULSE/PRIZM data
- The ability to tie an individual to a specific PRIZM segment, as well as the ability to tie that individual to a discrete correlated response value to any and all of the PULSE survey questions
- Other TBD data sources from Market Planning products (e.g. BRFSS, SMRB)

Consumer-provided communication preferences, e.g. opt-in/opt-out, channel preferences.

Message opportunity flags
- Cost savings, gaps and other opportunities generated by the Rules Engine Provider identification information at the claim level
- (e.g. Tax ID number) . . . not initially required to store more extensive physician information such as address, specialty, etc.

The exemplary system may also include the following additional value-add data sources.

Individual/Family benefit accumulator information (deductibles, OOPs, etc)

Member financial account information (HSA, FSA balances)

Member benefit plan design information (medical coverage benefits, drug formulary structure)

Cost Savings . . . not the Redbook stuff, but the output of

Program/intervention information (DM, wellness, web URL, etc.)

Health Risk Assessment
Behavioral Health Claims
Web clickstream from member/employee portal
Health Plan customer service interaction data
Disease Management interaction data
Wellness program interaction data
EAP interaction data
Short-term disability (STD), Long-term disability (LTD), Worker's compensation
Self-entered Personal Health Record (PHR) data Users should be able to allow users to mark and store favorites (see "My Bookmarks" on the sample dashboard, above) (CP 27).

From the dashboard, users will be able to obtain: A "quick-glance" state of user's healthcare with the ability to drill into details, learn more about a disease, surgery, drug, test, cost of treatment, treatment options, cost savings opportunities, etc. Quick Glance information is organized into My Care, Key Stats, My Expenses, and My News categories or regions.

The My Care category or region displays or provides access to—
  Conditions: Historical list of diseases rolled-up up into more easily understood groupings with user-friendly description. Details below.
  Medications: Historical list of drugs used by this person. Details below.
  Care History: Historical Overview of user's health claim usage provided in a graphical timeline by type of service. Details below.
  Preventative Services:
    Listing of and links to preventative services organized or searchable by age/gender, list the routine services person should have (tie into alerts/gaps in care); and whether or not they've had it without particular claims.
  Explicit link to Personal Health Statement (PHS): Summary and detailed list of claims for user (covered in separate specification). Provides utilization and cost information (a.k.a. "Informed Enrollment").
    Dashboard provides access PHS in interactive form (with filters by date, condition, user (if more than one)) and as a printable statement for specified time period.
  Each of the specific elements in My Care provides:
  Link to PHS: In addition to a specific link to the feature, each condition and medication provide a link into the detailed claims section of the PHS displaying that condition/medication.
  Links educational content (see below for details by type of data (condition, drug, etc.).

Figure 3:
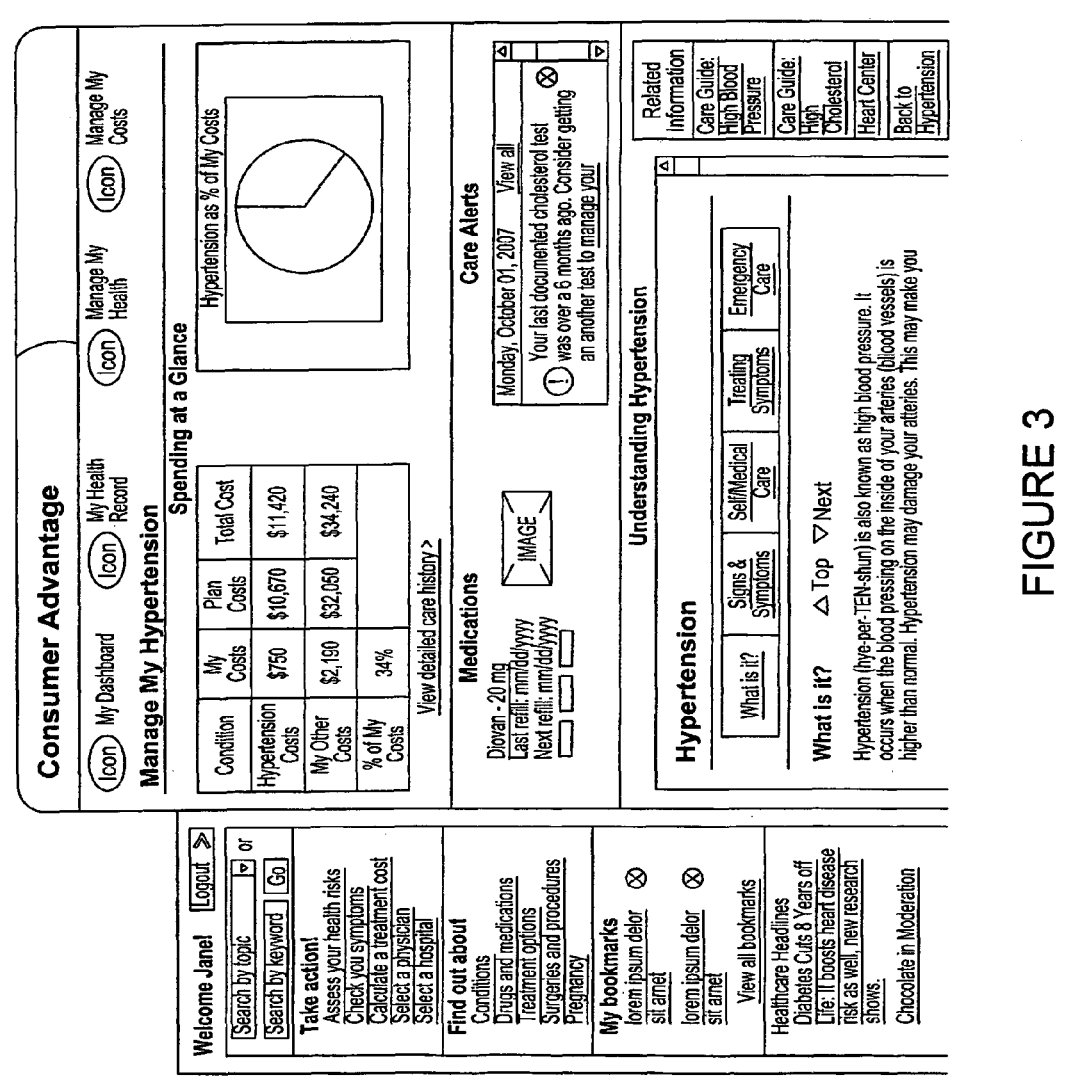

In some embodiments, condition or medication linked pages provide "mini dashboards" that integrate and personalize information about the specific condition or drug. See FIG. 3 for mock-up ideas.

My Stats (Key Stats): Vital Statistics based on information entered in the personal health records.

My Expenses: Summary of this user's healthcare spending (summary may include dependents' spending if the current user is the employee/key subscriber with dependents included as part of the plan). Details below.

My News:
My Care: Conditions Region
  Historical list of diseases rolled-up up into more easily understood groupings with user-friendly description
  Lists each unique condition (diagnosis group) for this patient with access to more details: educational information about the condition and claims detail related to it (list of specific health claims for the same condition as provided on the PHS)
  Displays all unique conditions and most recent treatment date ("Last Treated On" for each).
  Some embodiments identify and optionally suppress resolved or "old" conditions.
  If there are more conditions than can be displayed, some embodiments provide option and mechanism to view all conditions (e.g., only the first 5 conditions if total number exceeds space).
  Provide the same information and links as those shown directly on the dashboard.

Conditions are displayed as descriptions in layman's terms. To support this functionality, exemplary embodiment provides one or more tables of diagnosis or condition codes in association with layman terms and automatically looks up and substitutes layman terms for diagnosis or condition codes (or other medical jargon or terms of art.). In some embodiments, the original medical terms or codes are displayed to the user using a rollover or right click.

By default, display conditions in alphabetical order. Exemplary embodiment allows the user to sort conditions by date or condition name. For each condition, the exemplary embodiment provides links to Related claims for this condition (e.g., detailed claims shown on the Personal Health Statement) and to Specific health education content for the condition: Provide condition overview from the Health Encyclopedia.

FIG. 4: Input/Output/Manipulation/Error Handling

My Care Condition data is retrieved from the submitted insurance claims for the current user and/or from self-entered PHR data.

Input Sources for the conditions are derived from the Consumer Insights Database (CIDB) and may be driven by any/all of the following sources:
  Advantage database if one exists
  Direct customer claims feed (if no Advantage database)
  Personal Health Record (PHR)
  Input Fields: For the current person, use principal and secondary diagnosis codes (claims: inpatient, outpatient, office visits) to derive condition or Conditions (PHR).

PHR data may be used to capture self-entered conditions, drugs (e.g., non-prescription), conditions not claimed/covered by insurance; vital signs; more concurrent data Last Treated On Date: Most recent Date of Service from claims. See I/O Summary table.

The condition's link to Health Education content is derived from the Health Encyclopedia (Adam/Micromedex). Also see I/O Summary table. If the customer has not opted to purchase this module, no condition link should be provided.
  Creating the content link:
  Look-up content based on match of the most recent claim's specific diagnosis code for this condition
  If no condition is found in the encyclopedia, search by the condition's text and show the most relevant article (highest relevancy score)
  If the condition is not found by code or description, provide search feature when link is clicked with note that specific condition not found and suggestions for trying another search or alternative terms to select (or do not provide link for that condition).

Core Methodology
  Determining "Conditions"
    Diseases are grouped into conditions.
    Those conditions are associated with a layman's descriptions.

My Care—Conditions will share common grouping/ translation methods used by all the Consumer tools (e.g., Consumer Treatment Cost Calculator, PHS, PHR, etc.).

The precise grouping and translation methodologies are yet to be determined. Under consideration are Disease Staging Categories with supplemental laymen descriptions or portions of Thomson Medical Litigator software. Refer to the specifications for Layman's Translation as well as the PHR for additional information.

Details—My Care: Medications
Purpose of Feature
Historical list of medications
Lists each unique drug for this patient with access to more details: educational information about the it and claims detail related to it (list of specific health claims for the same medication as provided on the PHS)
Interface
Behavior:
Display all unique medications and most recent refill date ("Last Refill"), estimated next refill date (Next Refill"), days supply
identify and optionally suppress resolved or "old" medications Or identify "in use" drugs from those used in the past
If there are more medications than can be displayed, provide option and mechanism to view all (e.g., only the first 5 if total number exceeds space).
Provide the same information and links as those shown directly on the dashboard
By default, display medications in alphabetical order
Allow the user to sort by last refill date or name.
User sorts should persist throughout the session.
For each medication provide links to
Related claims (e.g., detailed drug claims shown on the Personal Health Statement)
Specific health education content for the medication: Provide drug overview article.
Optional "Proactive" Features:
Pre-check all "in use" medications for interactions with each other. Flag drugs with potential interactions. Flag should provide link to interaction checker results/warnings (see next item)
Provide explicit link to Drug Interaction Checker that is pre-populated with users "active" drugs (see I/O below).
Allow users to "turn off" those drugs that they don't want to include in check or to make additions (see CapMed's interface to the Micromedex Drug Interaction Checker found in the Consumer Sales Demo. Note—improved interface required).
Flag drugs where generic equivalent or other lower cost drugs are available (savings potential). Flag should provide link to Drug article for generic equivalent.
Navigation Considerations
Same as "Conditions" considerations above.
Integration Considerations: See overall design decisions, above.
FIG. 5: Input/Output/Manipulation/Error Handling
Medication: I/O Summary.
Medication: I/O Notes: See Core Methodology section below.
Core Methodology—
Identification of "active" drugs—those drugs for which a prescription is currently in use.

Figure 2:
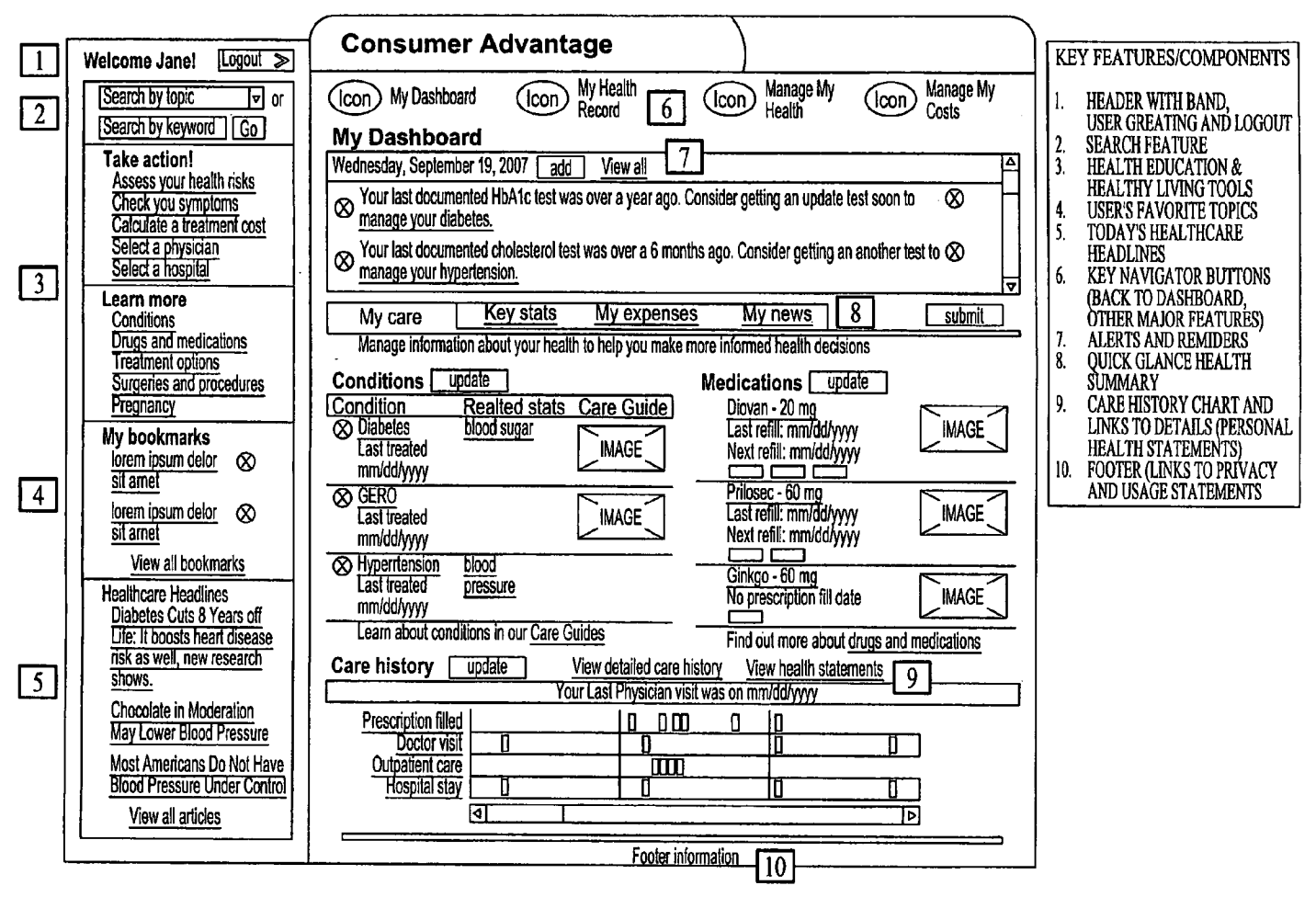
Figure 8:
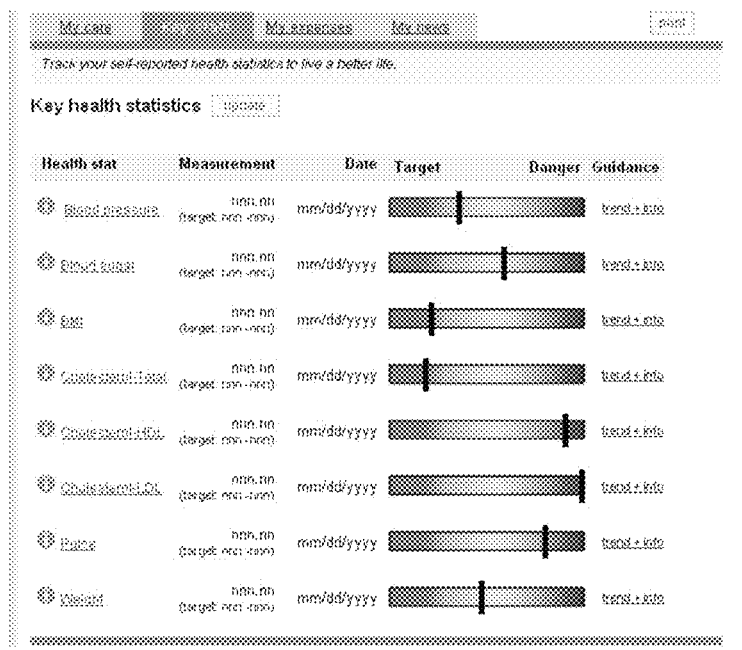

Drug Interaction Checker needs to support programmatic interface that can take in list of active drugs (by NDC code) and any other required fields (e.g., age/gender) and return interaction indication for each drug that has potential interaction.
Use of NDC code for drug look-up.
Details—My Care: Care History (CP 28.5)
Purpose of Feature
Care History: Historical Overview of user's health claim usage provided in a graphical timeline by type of service (CP 28.8)
Groups claims by type of service over time
Provides link to underlying claims detail in the Personal Health Summary
Rollover of data point displays brief overview of event (e.g., date, provider, service, cost)
Interface
Visual Design Mock-up:
See #9 in Sample Dashboard.
Style/Appearance Requirements: Follows dashboard requirements.
Behavior
Each type of service has links to the PHS to show the detailed claims
Provide "popup" detail for each data point on the timeline specifics about that service
Date, provider, condition (for Office, Outpatient or Hospital Service) or medication (Prescription), cost.
Link to the specific claim
Integration Considerations: See overall design decisions, above.
FIG. 6: Input/Output/Manipulation/Error Handling
Care History: I/O Summary.
Care History: I/O Notes
Suppress chart if no claims found for user. See I/O Summary above.
Core Methodology
Ability to group claims into service type categories (leverage work done in PHS).
Details—My Stats
Purpose of Feature
Lists user's most recently recorded vital signs and whether the results fall within standard target ranges if applicable.
Stats will be derived from:
The CapMed PHR
If the customer has not purchased the CapMed PHR, this information will be suppressed.
Interface
Visual Design Mock-up
A couple different visualizations of vitals are provided in FIGS. 7 and 8.
FIG. 7: Vital Signs 1
Vitals shown in the list of FIG. 7 are those to be included in the dashboard.
Height and Weight are included to support BMI calculations.
The visualization of FIG. 8 suggests a more graphical view of target range.
FIG. 8: Vital Signs 2
Style/Appearance Requirements:
Follows dashboard requirements.
Explore developing both textual and graphical way to view data (see ideas in Vital Signs FIG. 2 above).

Figure 10:
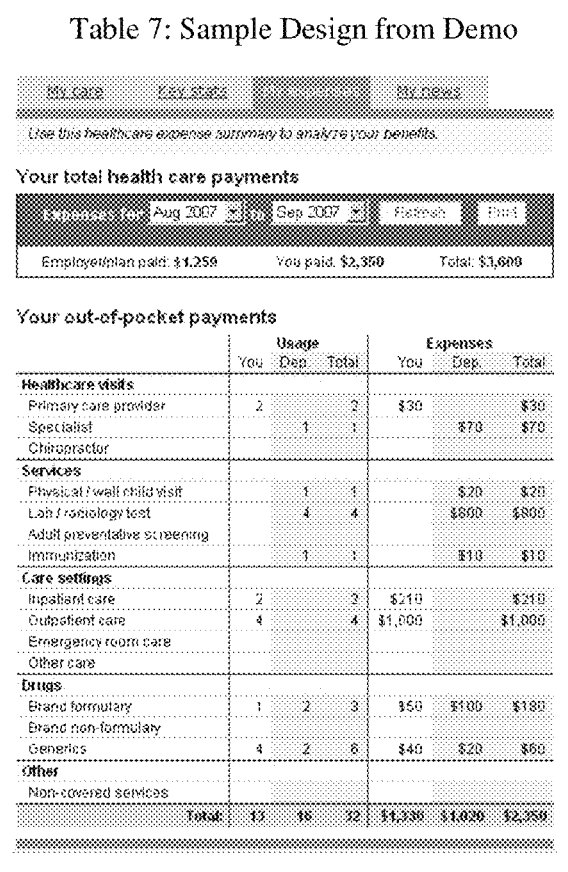
Figure 11:
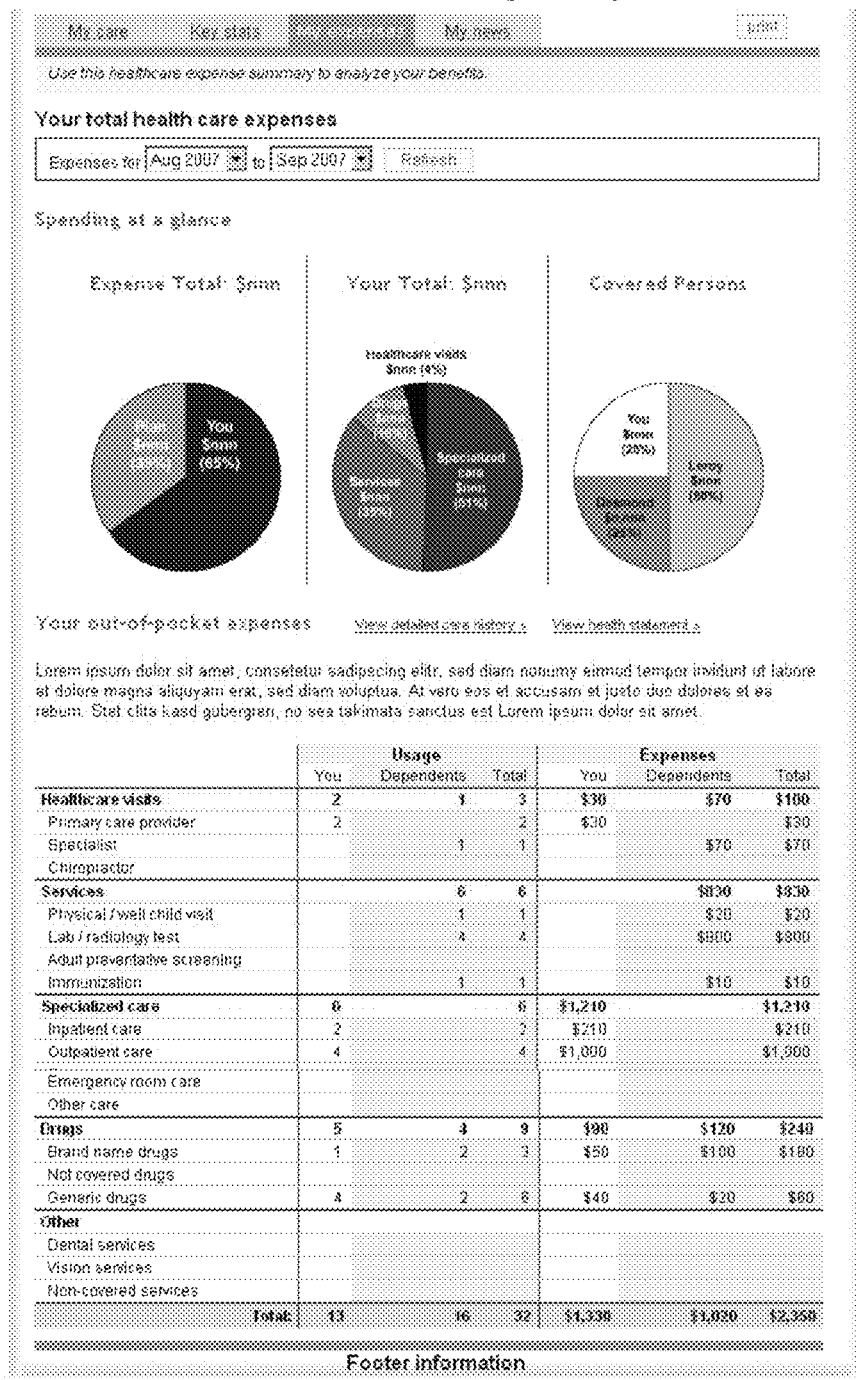

Behavior
For each vital sign, show details for the most recently recorded value (or date of service if lab data).
Show the details about each vital sign:
Value
Date recorded (or date of service)
Target range for that vital sign if available
Whether the value falls within the target range.
If there is more than one recording for that vital sign indicate if the most recent value is above or below the prior captured value.
Flag those vitals that are out of range.
If data is from the PHR, a link is provided from the dashboard to the PHR's vital signs.
Changes/adds to the vitals are done in the PHR and refreshed on the dashboard.
A quick link is provided from each vital sign to Health Education content for that metric.
Navigation Considerations
If the user navigates away from the dashboard while using "My Stats", the My Stats data is visible on return to the dashboard. Example, if the user views Health Education information linked from My Stats or a general healthcare link, on return to the dashboard, My Stats should be visible and displaying the most current data.
Integration Considerations:
See overall design decisions, above.
It also must integrate with CapMed PHR data and user updates.
FIG. 9: Input/Output/Manipulation/Error Handling
My Stats: I/O Summary
I/O Notes
Exact names of PHR input fields are to be defined.
When displaying the most recent vital value from the PHR, look across all dates for which vitals have been recorded.
Use the vital from the most recent date.
Note: users are not required to reenter all vitals each time they update a value. For example, on October 1 Jane may enter a new Weight, but not update her blood sugar. Blood sugar should NOT to be considered "unrecorded" without first checking PHR historical vitals for a recording on an earlier date.
Display only vital signs that are recorded (versus those that the user has opted not to capture).
Suppress vitals if no data found for user. See I/O Summary above.
Core Methodology
New methods/lookup table that provides determine industry standard target ranges for each supported vital sign where necessary taking into account the user's demographics such as age and gender.
Purpose of Feature
My Expenses provides a summary of total expenses (health plan paid, consumer paid, and total), use information by category of service. My Expenses aides the user in planning upcoming benefit needs (e.g., FSA, HSAs, plan selection) and determining overall healthcare expenses (e.g., for tax purposes). Much like the graphical Care History, My Expenses is a roll-up or interactive summary of cost and use information in the PHS. The exemplary embodiment relies on PHS capabilities to populate this information.
Interface
Visual Design Mock-ups:
FIG. 10: Sample Design from Demo
FIG. 11: Alternate Sample Design from Protosite
Style/Appearance Requirements: Follows dashboard requirements Behavior
Use the PHS to group claims into broad summary service categories and within that, service types.
Precise groupings will be defined by the PHS
User can filter the claims by date of service ranges (from mm/yyyy to mm/yyyy).
Default to most current calendar year to date.
User can filter the summary by Condition (also supports "Condition" summary pages if implemented), similar to ability to use Condition filter as shown on PHS in protosite.
Provide a tabular view of the Summary
Optionally, provide a graphical view of expenses as suggested in the Protosite example above.
Shows information for the current user and dependents, if any.
If single coverage for user only, Usage and Expense breakouts and charts show just a single total for that user (no need for "You" and "Dependents" as shown below).
Allow the user to print the Summary.
When printing the summary, include the name of the current user.
Each type of service has links to the PHS to show the detailed claims
If user clicks link, pre-filter PHS to reflect the filters in place on the summary (e.g., time range, type of service and condition)
Integration Considerations: Data and functionality must integrate with PHS capabilities.
FIG. 12: Input/Output/Manipulation/Error Handling
My Expenses: I/O Notes
Suppress chart if no claims found for member. See FIG. 12.
Only include "dependent" information if the current user is the primary member. If this is a dependent's dashboard view, follow same rules as if single member (w/o dependents): show "totals" only.
Include the current user's name on the summary for clarification.
No claims—for user or dependents: Display message that no claims were found (this may occur because of the filter selections or no data exists).
Much of the above actual I/O logic should be handled by the PHS module with the dashboard interface supplying the User's "family" or subscriber "ID" as well as filtering parameters that limit the number and types of reported claims.
Note: much of this logic should be clarified during development work for Health Equity.
Core Methodology
Ability to group claims into service categories (leverage work done in PHS) and conditions.
Use PHS capabilities to feed this report.
Ability to link claims across "family" to identify "you" and associated dependents, if any.
Issue: identify/clarify i/o fields and methods to do this or defer to PHS module to handle this.
Details—My News (CP 28.7)
Purpose of Feature
User can keep up to date on the latest healthcare news and research related to 1) specific conditions for this user, 2) health care topics of particular interest to the user, 3) today's latest healthcare news.

News is based on several capabilities:

Article List: links to articles (personalized)

Search of News Archives

List of links to articles based on search results

News Article

Today's Headlines (list of links for just today; no personalization)

Access to personalized articles would be from tab or menu option on the dashboard It is possible that, rather than having a standalone news "tab", news articles are integrated with other user content (e.g., with Condition or Drug information) or from a News page accessed from a menu navigator (e.g., see Headlines example). However, that summary News page would have similar capabilities as the "My News" tab regardless of navigation.

Behavior: The Dashboard or news service provides the user with a way to subscribe to content based on topics of interest and/or automatically create a list of articles based on the user's conditions and drugs (as found on the My Care tab). The exemplary system auto-subscribe the user to receive articles by matching conditions to news articles topics/categories. It also allows the user to also constrain news by time (e.g., today only, past week, month, year, all relevant articles).

Dashboard will provide Article Lists (links) of interest to user. The list will categorize the links by:

The user's conditions (if any)

Topics or categories of interest to the user (via user's subscription information)

If the user has no areas of interests (conditions or subscriptions), the user will see all healthcare headlines for today in the default order of the news feed Article Lists should include visual images (thumbnail if necessary).

The list of articles provides a short description of the article, the article source and date of posting. The list of articles also reflects news for the past <N days, month, year>.

Search: My News link page and any articles also includes a search capability to find articles by keyword, specific topic or by specific category (options based on Thomson's My Daily News feed) Optionally, allow the search to be constrained by a time frame (today, last week (last 7 days), last month (last 30 days), last year (last 365 days), custom time frame (mm/dd/yyyy-mm/dd/yyyy), all articles). List of Search results includes article name, topic, link to article, short description of article, date of article author and source. Search results should be sorted by date in descending order (most recent articles to oldest)

Integration Considerations:

News feed topics/categories can be mapped to key disease conditions and drugs

News service subscription service options integrated into user "profile" capabilities Customer's non-standard news service integrated into link(s) on dashboard My News: I/O Notes Details of personalization from user's conditions, medications and specific topics of interest should be used to search and customize news feed articles Similarly consider allowing user or system to constrain news archive searches by a time frame If the user has a specific time frame preference, some embodiments save it and use it as the default for future searches.

Alerts, Reminders and Messages

Purpose of Feature

Alerts: Timely, personalized, actionable alerts about key health issues related to that person's relevant preventative services (e.g., annual physical, mammogram, and immunizations), disease management, medications, upcoming tests, cost savings, etc.

Messages: Timely messages/reminders set by the user or posted by the customer

Customer Messages and Contact Information

A separate area/linking mechanism should be provided for customers to post important messages to all or select groups of users Customers also need link and message area to post Contact Information and Frequently Asked Questions (FAQ)

Interface

If listed together, the user should be able to visually distinguish between system-defined alerts and user-defined messages.

If there are no alerts or user-defined reminders, show message that there are no alerts/messages (do not suppress alert area on dashboard).

The exemplary embodiment displays alerts first followed by any user defined message, with alerts displayed or listed in order (alphabetically) by condition name. In some embodiments, the alerts are displayed in order medical severity, for example most severe to least severe. Alert text should provide a message that is in layman's terms. Alerts that have text referring to a specific test, lab result, condition or healthcare term provide a pop-up or rollover message with a short description about that term (as found in the Healthcare Encyclopedia) The text includes a statement about the issue, why it's important and action to be taken by the user ("call to action" format; see Requirements). In the exemplary embodiment, users will have the ability to turn off Alerts.

User-Defined Messages

User-defined reminders will be pulled by the dashboard from the CapMed PHR

If the customer has not purchased the PHR or the user does not have messages, then no user-defined messages will be available on the dashboard.

The ability to set/turn-off user-defined reminders is available only if the CapMed PHR is available.

Provide a link to the CapMed PHR Message area to allow the user to manage messages.

If listed together with Alerts, reminders should appear after alerts.

If the CapMed PHR is not licensed, provide the user with a "Notes" area to track key information such as Physician, Insurance information Customer-Defined Messages The dashboard will provide a link and message page for customers to post important messages to their users.

Usage examples:

The message page should provide standard navigation back to the main dashboard view The message page should be follow branding and style of CDDS Provide customer with style sheet or tool to integrate message The customer should be able to designate which users should see message (e.g., all or set population)

Project Details—Access Health Education/Healthy Living Tools

Purpose of Feature

The dashboard will provide the user with access to a set of health education and wellness tools. Education tools can be used to research terms, diseases, surgeries, tests, medications etc.

In addition, these same education tools serve as the underlying resource for personalized links Wellness tools allow the user to monitor key metrics and guidance (e.g., BMI calculator, Target Heart Rate Calculator)

General search capability across the content that returns links to one or more articles. The search capability is available from: The dashboard, Search results list (see below), Article pages, Other pages where appropriate (e.g., Manage My Condition page)

By default, the content is provided by Thomson-owned through existing Micromedex/Nexcura content or via 3rd party A.D.A.M. content. However, the customer has the option to swap in content from their vendor of choice, for example via a preference definition.

Interface

Visual Design Mock-up—Sales Demo Content Navigator
Behavior

Dashboard will provide links to content, organized by key topical areas

Some embodiments blend content to define a "one stop shop" article—e.g, this can entail merging related information for a drug from across content modules such as: Drug Notes, Images, Interaction, Detailed Articles. Provide links to related articles next to the article. Related links will cross licensed content types (not confined to just the encyclopedia for example). Example: User searches encyclopedia for Diabetes. A related links navigator would contain links to the Diabetes Care Guide, the Decision Assist or Nexcura links for diabetes, as well as other relevant articles within the encyclopedia To blend related education content, for example see Condition-Specific mock-up.

Search

General search capability across the content that returns links to one or more articles:
 User-specified keyword(s)
 Topical Area (e.g., Diseases and Conditions, Tests)
 User should be able to refine the keyword search by a topical area.
 List of articles should provide quick summary, topical area, relevancy (see ADAM demo for example)
 List should be ordered by relevancy score
 Search capability should appear on the results list as well.
 If no articles found,
 Display message to that effect
 Offer option to search again
 Hints: list of similar terms ("did you mean < . . . >")
 Navigation Considerations
 Integration Considerations: As noted above
 Merging separate content modules into once article or reference page
 Searching into single or multiple content modules
 Turning of links or searches into unlicensed modules (by customer)
 Input/Output/Manipulation/Error Handling To create links to specific content modules, such as the "Surgeries and Procedures". In the exemplary embodiment this entails determining Article ID (product ID) for each and building up or defining a URL that then contains the ID (if ADAM hosts). Example of URL:
 https://ssl.adam.com/content.aspx
  site=medstatadam.com&productId=13

The URL can then be used to retrieve the content it references.
 Core Methodology
 Access to Decision Making Tools (CP 32-35)
 Purpose of Feature
 Dashboard will provide access to decision making tools:
 Consumer Treatment Cost Calculator (CTTC)
  Refer to the CTTC requirements, design and prototype for additional details.
  Provider Selection (Physician and Hospital)—DEFERRED
  Health Plan Selection–DEFERRED (except for PHS)
 Interface
 Visual Design Mock-up
  Access to the CTCC will be via a link from the dashboard.
 Style/Appearance Requirements
  The CTCC should integrate into the dashboard—with the ability to take on the same "skin", branding and fit within standard navigation schemes
 Behavior
  When user selects link to CTCC, open the customer-selected CTCC
   Provide the ability to pass the user information to the CTCC to (e.g., Person ID/member ID) so that the CTTC recognizes the user and can pre-populate known fields, simplifying user entry in the calculator.
 Navigation Considerations
  CTCC should be able to be housed within the dashboard content window
  The dashboard should provide the option to let the user open the CTCC in a new window (to provide more real estate to the CTCC)
   If the CTCC opens in a new window, it should be very clear to the user how to return to the Dashboard.
 Integration Considerations
  The dashboard should accommodate other 3rd party TCC's selected by the customer.
 Input/Output/Manipulation/Error Handling
  I/O Notes: Pass user identifier information need by the CTTC to "recognize" the user so that the CTTC can pre-populate key CTTC user-specific information.
 Core Methodology
 Project Details—Access to Personal Health Statement (CP 28.9)
 Purpose of Feature
  In addition to an overview of a user's healthcare, the dashboard will provide the ability to drill into underlying detail ("My Health in Detail") via the Personal Health Statement (PHS) and, optionally, the Personal Health Record (PHR). The PHS and PHR are described in the next two sections
  Patient Health Statement (PHS; summary of medical insurance claims)
   Requirements are still under development. But user should be able to create and print a summary of medical insurance claims information. Refer to the "My Expenses" for dashboard links into the PHS.
   Dashboard version should allow interactive view that allows user to filter by time period and see both summary and detailed claim views (as shown under My Expenses).
  Interface
   Access to the PHS will be via a link from the dashboard and from within the My Expenses modules.
  Style/Appearance Requirements
   The PHS integrates into the dashboard—with the ability to take on the same "skin", branding and fit within standard navigation schemes. The PHS should support printing as a PDF.

Behavior

When user selects link to PHS, create default report for user (based on default time period range (current quarter); TBD)

Navigation Considerations

Integration Considerations

Terms/roll-ups for Conditions and Medications (and procedures) should match between the dashboard and PHS.

I/O Notes: Pass user information required to create default report. Further details deferred until completion of requirements and PHS design.

FIG. 13 shows Diagnosis Codes.
FIG. 14 shows Procedure Codes.
FIG. 15 shows Drug Codes.
FIG. 16 shows Diagnosis Codes.
FIG. 17 shows Procedure Codes.
FIG. 18 shows Drug Codes.

Alerts and Reminders—Replace the clinical condition with layperson's terminology. See example.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A computer device, comprising:
a display configured to show thereon a graphical user interface (GUI);
a communications interface;
a computer-readable memory; and
a processor operatively connected with the display, the communications interface and the computer-readable memory, the processor configured to perform actions comprising:
receiving, via the communications interlace, personal health records data for a user;
receiving, via the communications interface, personal health care spending data for the user;
receiving, via the communications interface, potential health treatments data for the user;
automatically populating personal health records information with health claims history information for the user based on the received personal health records data;
determining summarized personal health spending information for the user based on the received personal health care spending data for the user;
requesting, via the communications interface, best practice medical treatment data based on the received personal health records data for a user and the received potential health treatments data for a user;
customizing potential health treatments information for the user based on the received potential health treatments data, the received personal health records data for the user, and the best practice medical treatment data; and
displaying a dashboard for the user on the GUI, the dashboard simultaneously showing the personal health records information for the user, the summarized personal health spending information for the user, and the customized potential health treatments information for the user.

2. The computer device of claim 1, wherein the received personal health records data for the user includes treatment history for the user, medication records for the user, and the health claims history information for the user.

3. The computer device of claim 1, wherein the received potential health treatments data for the user includes potential medications information and potential health costs information.

4. The computer device of claim 1, wherein the processor is configured to perform a further action of requesting, via the communications interface, the potential health treatments data for the user based on user preferences.

5. The computer device of claim 1, wherein;
the processor is configured to perform the further action of determining personal health statistics for the user based on the received personal health records data for the user; and
for the action of displaying the dashboard for the user on the GUI, the dashboard simultaneously further shows the personal health statistics for the user.

6. The computer device of claim 1, wherein:
the processor is configured to perform the further action of determining personalized alerts for the user based on the received personal health records data for the user; and
for the action of displaying the dashboard for the user on the GUI, the dashboard simultaneously further shows the personalized alerts for the user.

7. The computer device of claim 1, wherein the received personal health records data for the user further includes dependent health records data for a dependent of the user.

8. The computer device of claim 1, wherein the computer device is a mobile device and the communications interface includes a wireless communications interface.

9. The computer device of claim 1, wherein:
the processor is configured to perform the further action of providing one or more detailed tools for the user; and
for the action of displaying the dashboard for the user on the GUI, the dashboard simultaneously further shows one or more user-selectable tool options for the one or more detailed tools.

10. The computer device of claim 9, wherein the one or more detailed tools are selected from the group consisting of a healthcare spending tool, a drug interaction tool, a vital signs tool, and a personalized alerts tool.

11. The computer device of claim 10, wherein the healthcare spending tool is configured to allow the user to interact with the GUI for the processor to perform further actions selected from the group consisting of:
comparing health plan coverage options for the user;
estimating health care costs for the user;
receiving money-saving personalized alerts; and
comparing projected out-of-pocket expenditures for major healthcare events for different providers.

12. The computer device of claim 11, wherein the money-saving personalized alerts comprise an indication that a cheaper, generic drug may be substituted for an active drug for the user.

13. The computer device of claim 10, wherein the drug interaction tool is pre-populated with a list of active drugs for the user.

14. The computer device of claim 13, wherein the processor is further configured to perform the action of allowing the user to make additions and subtractions to and from the pre-populated list of active drugs for the user.

15. The computer device of claim 10, wherein the vital signs tool is configured to show most recent vital signs for the user, an indication whether any of the most recent vital signs falls into a target range for the vital sign, and, if any of the most recent vital signs fall outside of the target range for the vital sign, flags indicating any of the most recent vital signs that fall outside of the target range for the vital sign.

16. The computer device of claim 10, wherein the personalized alerts tool is configured to provide alert information selected from the group consisting of preventative services, reminders created by the user, and healthcare news chosen based on personal information for the user.

17. The computer device of claim 10, wherein the personalized alerts tool is configured to:
   determine, based on a review of the user's health claims history information, if a relevant drug has been prescribed; and
   based on the determination, provide an indication that a relevant drug is typically prescribed to persons with similar health claims history information as the user.

18. A method for providing personal health information for a user, the method comprising;
   receiving, by a processor, personal health records data for the user;
   receiving, by the processor, personal health care spending data for the user;
   receiving, by the processor, potential health treatments data for the user;
   automatically populating, by the processor, personal health records information with health claims history information for the user based on the received personal health records data;
   determining, by the processor, summarized personal health spending information for the user based on the received personal health care spending data for the user;
   requesting, by the processor, best practice medical treatment data based on the received personal health records data for a user and the received potential health treatments data for a user;
   customizing, by the processor, potential health treatments information for the user based on the received potential health treatments data, and the received personal health records data for the user, and the best practice medical treatment data; and
   displaying, by the processor, a dashboard on a graphical user interface (GUI), the dashboard simultaneously showing the personal health records information for the user, the summarized personal health spending information for the user, and the customized potential health treatments information for the user.

19. The method of claim 18, wherein the received personal health records data for the user includes treatment history for the user, medication records for the user, and the health claims history information for the user.

20. The method of claim 18, wherein the received potential health treatments data for the user includes potential medications information and potential health costs information.

21. The method of claim 18, further comprising requesting, by the processor, the potential health treatments data for the user based on user preferences.

22. The method of claim 18, wherein, for receiving personal health records data for the user, the personal health records data includes dependent health records data for a dependent of the user.

23. The method of claim 18, further comprising providing, by the processor, one or more detailed tools for the user, wherein, for displaying the dashboard on the GUI, the dashboard simultaneously further shows one or more user-selectable tool options for the one or more detailed tools.

24. The method of claim 23, wherein, for providing one or more detailed tools, the one or more detailed tools are selected from the group consisting of a healthcare spending tool, a drug interaction tool, a vital signs tool, and a personalized alerts tool.

25. A computer device, comprising:
   a display configured to show thereon a graphical user interface (GUI);
   a communications interface;
   a computer-readable memory; and
   a processor operatively connected with the display, the communications interface and the computer-readable memory, the processor configured to perform actions comprising:
      receiving, via the communications interface, personal health records data for a user;
      receiving, via the communications interface, potential health treatments data for the user;
      automatically populating personal health records information with health claims history information for the user based on the received personal health records data;
      requesting, via the communications interface, best practice medical treatment data based on the received personal health records data for a user and the received potential health treatments data for a user;
      customizing potential health treatments information for the user based on the received potential health treatments data, the received personal health records data for the user, and the best practices medical treatment data;
      providing one or more detailed tools for the user; and
      displaying a dashboard for the user on the GUI, the dashboard simultaneously showing the personal health records information for the user, the customized potential health treatments information for the user, and one or more user-selectable tool options for the one or more detailed tools.

26. The computer device of claim 25, wherein the one or more detailed tools are selected from the group consisting of a healthcare spending tool, a drug interaction tool, a vital signs tool, and a personalized alerts tool.

* * * * *